United States Patent
Shojaei et al.

(10) Patent No.: US 6,772,801 B1
(45) Date of Patent: Aug. 10, 2004

(54) FLUIDIZATION OF PARTICLES FOR ENCAPSULATION IN ORAL DOSAGE PHARMACEUTICAL PRODUCTS

(75) Inventors: Amir H. Shojaei, Gaithersburg, MD (US); Benjamin Thomas Kibalo, Gaithersburg, MD (US); Scott A. Ibrahim, Burtonsville, MD (US)

(73) Assignee: Shire Laboratories, Inc., Rockville, MD (US)

( * ) Notice: Subject to any disclaimer, the term of this patent is extended or adjusted under 35 U.S.C. 154(b) by 0 days.

(21) Appl. No.: 10/437,397

(22) Filed: May 14, 2003

(51) Int. Cl.[7] ................................................. B65B 1/20
(52) U.S. Cl. ............................... 141/11; 141/4; 141/67; 141/70; 141/129
(58) Field of Search ............................ 141/4–8, 11, 67, 141/69, 70, 129, 192, 198; 222/345, 346, 368, 636, 189.06; 356/101, 106, 107

(56) References Cited

U.S. PATENT DOCUMENTS 4,640,322 A * 2/1987 Ballester ........................ 141/5

| 5,826,633 A | 10/1998 | Parks et al. |
| 6,267,155 B1 | 7/2001 | Parks et al. |
| 2001/0047837 A1 | 12/2001 | Parks et al. |
| 2002/0148527 A1 | 10/2002 | Parks et al. |

* cited by examiner

Primary Examiner—Timothy L. Maust
(74) Attorney, Agent, or Firm—Edell, Shapiro & Finnan, LLC; M. Elisa Lane

(57) ABSTRACT

Encapsulated oral dosage pharmaceutical products are produced utilizing a system including a hopper and a dosator, where the hopper receives particles having irregular geometries and sizes greater than about 100 $\mu$m for delivery to the dosator. A gaseous fluid is directed into the hopper to fluidize particles within the hopper so as to minimize or eliminate the formation of voids within the bed of particles disposed within the hopper. The fluidization of the particles within the hopper maintains a substantially continuous and uniform flow of particles from the hopper to the dosator, which results in the formation of encapsulated products with desirable weights and particle size distributions.

11 Claims, 2 Drawing Sheets

FLUIDIZATION OF PARTICLES FOR ENCAPSULATION IN ORAL DOSAGE PHARMACEUTICAL PRODUCTS

BACKGROUND OF THE INVENTION

1. Technical Field

The present invention pertains to improvements in methods and apparatus for encapsulating particulate material, in particular, microparticulates and granules, in the manufacture of pharmaceutical products for oral dosage or delivery.

2. Discussion of the Related Art

Various pharmaceutical products are packaged in the form of capsules for oral dosage and controlled release of a pharmaceutically active composition within an individual's body. Oral dosage pharmaceutical capsules are typically filled with microparticulate material or granules on the order of several microns in dimension (e.g., greater than about 100 $\mu$m). The encapsulated particles typically contain a select amount of one or more pharmaceutically active compositions along with one or more inert excipient materials. In a typical encapsulation process, a source of particulate material or particles to be encapsulated is transferred by gravity from a hopper to a dosator, where the dosator determines the amount of particles to be added to each capsule. The dosator transfers the requisite amount of particles into an open capsule (e.g., an open shell portion of the capsule), and the open capsule is then sealed (e.g., by placing a shell cap over the open shell portion filled with particles).

Depending upon the physical attributes of the particles to be encapsulated for the oral dosage product (e.g., variations in particle size, tackiness of the particulate material, irregularities in particle surface geometries, etc.), problems may occur in the transfer of the particles from the hopper to the dosator. When utilizing a pharmaceutical material that is difficult to encapsulate, voids can be created in the hopper at locations previously occupied by particles transferred into the dosator, where the particulate material remaining within the hopper may not readily fill such voids. This can be a significant problem, for example, when the particles to be encapsulated have non-spherical and irregular geometric surfaces, which causes the particles to frictionally adhere to each other, rather than sliding with respect to each other, as the particles are gravity fed from the hopper to the dosator. The generation of voids within the hopper in turn leads to significant and undesirable deviations in the amount of particles transferred to the dosator and, thus, to the pharmaceutical capsules being produced. In preparing product capsules with particulate material that is difficult to encapsulate, the capsules tend to decrease in fill weight during the production process, with unfilled voids increasing in size until very little or no particles are transferred from the hopper to the dosator.

Attempts at overcoming the aforementioned problems utilizing conventional methods result in further particulate flow problems within the hopper and/or degradation of desirable properties of the particles. For example, if the hopper is vibrated in an attempt to eliminate voids within the particle bed, the particles can become compacted, particularly when the hopper circumference is reduced (e.g., funnel shaped) near the outlet, resulting in reduced or no flow of particles from the hopper into the dosator. Mechanical stirring within the particle bed to inhibit the formation of voids can lead to crushing of particles, which reduces particle size from a desired range and results in undesirable deviations in the dissolution profiles for resultant oral dosage capsule products.

Thus, an improved system and method is desirable for ensuring accurate dosage amounts of particulate material in the production of oral dosage pharmaceutical products, particularly capsule products having particle dimensions greater than about 100 $\mu$m and irregular and non-spherical shaped geometries.

OBJECTS AND SUMMARY OF THE INVENTION

Therefore, in light of the above, and for other reasons that become apparent when the invention is fully described, an object of the present invention is to manufacture oral dosage pharmaceutical products, such as capsule products, including particles with irregular and non-spherical shaped geometries.

It is another object of the present invention to manufacture oral dosage pharmaceutical products including particles with dimensions greater than about 100 $\mu$m.

It is yet another object of the present invention to manufacture oral dosage pharmaceutical products including particles with irregular geometries where the products do not deviate significantly from a desired or target fill weight.

It is a further object of the present invention to manufacture oral dosage pharmaceutical products including a substantially uniform blend of particles with varying irregular shapes and sizes.

The aforesaid objects are achieved individually and/or in combination, and it is not intended that the present invention be construed as requiring two or more of the objects to be combined unless expressly required by the claims attached hereto.

According to the present invention, oral dosage pharmaceutical products are produced including particles with irregular geometries utilizing a system including a hopper and a dosator. The hopper receives particulate material that includes particles having irregular geometries as defined by a roundness value of no greater than about 0.40. A gaseous fluid is directed into the hopper to fluidize at least some of the particles within the hopper. A selected amount of the particulate material is transferred from the hopper into the dosator, and an oral dosage pharmaceutical product is formed from the selected amount of particulate material expelled from the dosator. The formation of voids within the particles disposed within the hopper is prevented or minimized by fluidizing particles within the hopper prior to delivery to the dosator. Oral dosage pharmaceutical capsules are formed in accordance with the present invention that contain particles of irregular geometries and sizes greater than about 100 $\mu$m while substantially maintaining the capsule weight and particle size distribution of each capsule within a desired range. Preferably, a majority of the capsules in a production batch do not deviate from a target fill weight by more than about 15%, and the average fill weight of a single capsule in the batch does not deviate from the target fill weight by more than about 10%.

The above and still further objects, features and advantages of the present invention will become apparent upon consideration of the following detailed description.

DETAILED DESCRIPTION OF THE PREFERRED EMBODIMENTS

Figure 1:
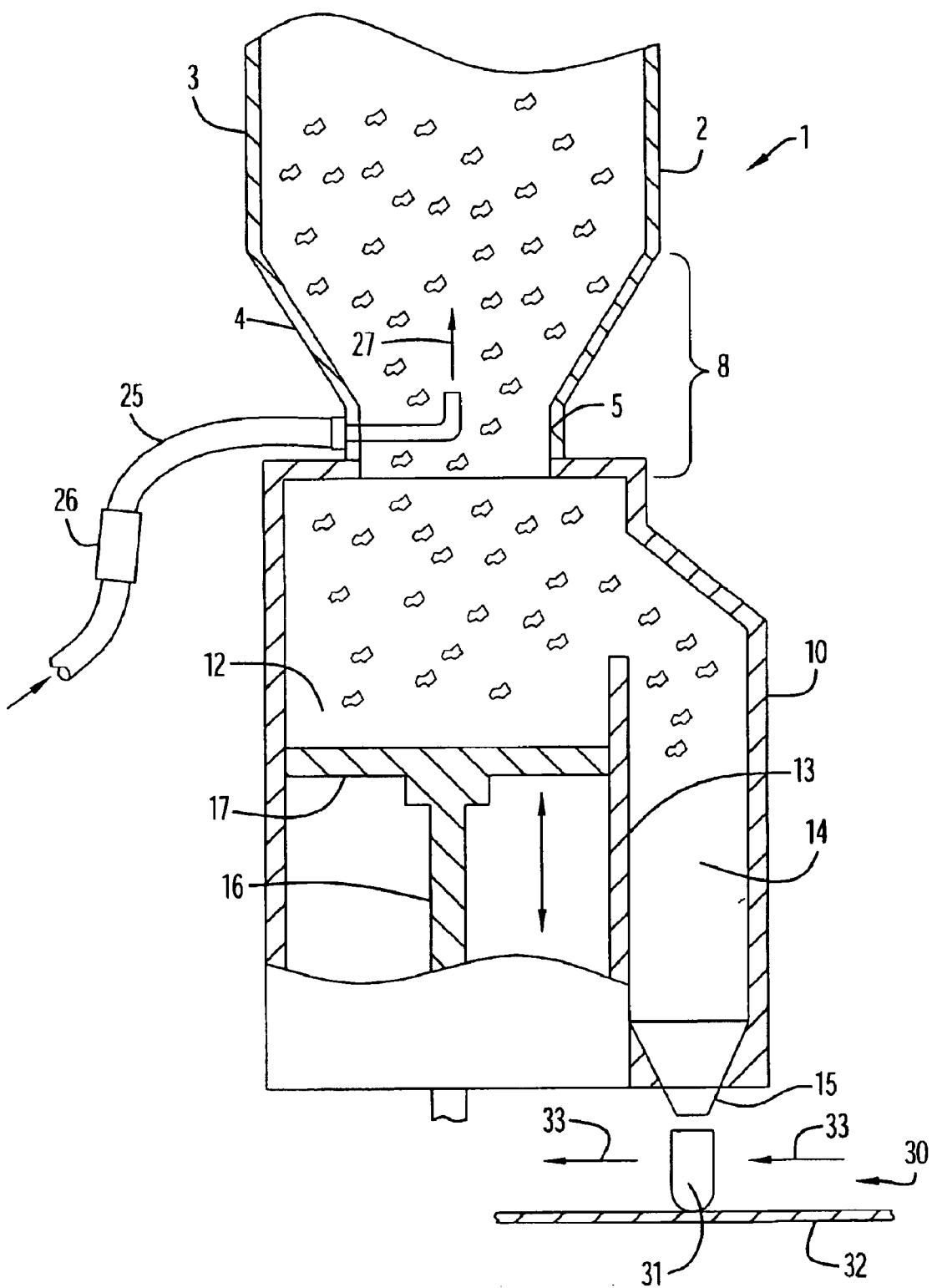
FIG. 1 depicts an exemplary embodiment of an encapsulating system in section for filling oral dosage pharmaceutical capsules with particles in accordance with the present invention.

As noted above, problems occur in manufacturing oral dosage pharmaceutical capsule products including particles with irregular geometries, particularly when such particles increase in dimension. The term "irregular geometry", as used herein, refers to a generally non-spherical geometry. In particular, voids tend to form in the hopper due to particles with irregular geometries frictionally engaging with each other rather than sliding toward the hopper outlet for delivery into the dosator, which in turn results in erratic and non-uniform dosage amounts for the capsules formed.

The present invention addresses the problems encountered with manufacturing oral dosage pharmaceutical capsule products that contain particulate material including one or more active ingredients and excipient and having irregular geometric configurations. In particular, the capsule products contain particles that have a roundness that deviates significantly from a spherical or other well-rounded and smooth configuration. The capsule products further contain at least some particles with dimensions that are greater than at least about 100 $\mu$m. In addition, capsule products are manufactured that contain a variety of irregular geometric configurations and/or size dimensions.

Roundness of a particle of interest can be described in terms of sphericity, which is the degree of abrasion of a particle as shown by the sharpness of its edges and comers. Sphericity has been expressed by Wadell (1932) as the ratio of the average radius of curvature of several edges or corners of a particle to the radius of curvature of the maximum inscribed sphere (or to one-half the nominal diameter of the particle). See, e.g., Bates, R. L. and Jackson, J. A., 1980, *Glossary of Geology*, 2nd *Edition*. Falls Church, Va., American Geological Institute, the disclosure of which is incorporated herein by reference in its entirety. In particular, a sphericity value is useful in providing an indication as to the degree in which a particle of interest deviates from a sphere. For example, sphericity may be defined as the ratio of the surface area of a sphere, which has the same volume as the particle of interest, to the particle of interest. The maximum sphericity value (e.g., for a sphere) is 1, and the sphericity value decreases the more the particle of interest deviates from a spherical geometry. Pharmaceutical capsule products manufactured in accordance with the present invention preferably include a majority of particles having a sphericity value of no greater than about 0.7.

Another useful technique for determining particle roundness involves a visual comparison of the particle of interest with a series of roundness classifications as developed by Krumbein et al. See e.g., Krumbein, W. C. and L. L. Sloss (1951) *Stratigraphy and Sedimentation*. $2^{nd}$. Ed. W. H. Freeman and Company, London, the disclosure of which is incorporated herein by reference in its entirety. A range of roundness values have further been developed to correspond with these roundness classifications. See, e.g., Bates, R. L. and Jackson, J. A., 1980, *Glossary of Geology*, 2nd *Edition*. Falls Church, Va., American Geological Institute. In particular, the roundness class as developed by Krumbein et al. includes the following classifications: well-rounded (roundness value between 0.60 and 1.00), rounded (roundness value between 0.40 and 0.60), subrounded (roundness value between 0.25 and 0.40), subangular (roundness value between 0.15 and 0.25), and angular/very angular (roundness value between 0.0 and 0.15). Pharmaceutical capsule products manufactured in accordance with the present invention preferably include a majority of particles that have a roundness value of no greater than about 0.40 (i.e., subrounded to angular/very angular). Most preferably, the pharmaceutical capsule products will include a majority of particles that have a roundness no greater than about 0.25 (i.e., subangular to angular/very angular).

Oral dosage pharmaceutical capsule products manufactured in accordance with the present invention preferably include a majority of particles having dimensions of at least about 100 $\mu$m. More preferably, the capsule products include a majority of particles having dimensions in the range of between about 125 $\mu$m and about 1,000 $\mu$m (1 mm). Most preferably, the capsule products include a majority of particles having dimensions in the range between about 185 $\mu$m and about 400 $\mu$m.

The occurrence of voids within the particle bed of the hopper, and resultant problems with capsule production, is minimized or eliminated in accordance with the present invention by fluidizing at least some of the particles with irregular shapes or geometries (e.g., particles with a roundness value of no greater than 0.40) within the hopper to facilitate substantially even and uniform flow of the particles through the hopper to the dosator. Preferably, fluidization of particles within the hopper is achieved by directing at least one gaseous fluid (e.g., air or an inert gas such as nitrogen) in one or more suitable directions (e.g., countercurrent and/or cross flow) through the particle bed within a gravity fed hopper to cause one or more groups of particles within selected locations of the particle bed become fluidized or flow in a manner that resembles a dense fluid within the hopper. Fluidization of at least some of the irregular shaped particles within the particle bed results in particles filling in areas previously occupied by particles exiting the hopper so as to prevent the formation of voids within the particle bed. In particular, it is desirable to establish a minimum fluidization velocity for the gaseous fluid directed through the particle bed so that the drag force caused by the fluid acting on selected particles is balanced with respect to the gravitational forces acting on the particles, resulting in the fluidization of the selected particles. The minimum fluidization velocity depends on a number of physical parameters of the particles and gaseous fluid, such as particle sphericity, particle dimensions, and particle and fluid densities. The minimum fluidization velocity as well as general flow characteristics through a packed bed are described in detail in McCabe, Smith and Harriott, *Chemical Engineering Series $5^{th}$ ed.: Unit Operation of Chemical Engineering*, McGraw Hill, 1933, the disclosure of which is incorporated herein by reference in its entirety.

An exemplary system for manufacturing oral dosage pharmaceutical capsules is depicted in FIG. 1. System 1 includes a hopper 2, a dosator 10 disposed below the hopper to receive particles transferred from the hopper and to control the amount of particles dispensed to individual capsules, and a capsule station 30 that selectively orients a plurality of capsules with one or more outlets of the dosator to facilitate filling of the capsules with particles. The hopper, dosator and capsule station may be obtained from any conventional or other suitable types of encapsulation equipment including, without limitation, a CD-5 encapsulator unit commercially available from Romaco (N.J.).

The hopper includes an upper cylindrical section 3 with an opening at the top that serves as a hopper entrance to receive particulate material. Extending from the upper cylindrical section is a tapered or funnel section 4 that reduces in transverse dimension to a spout S disposed at the lower end of the hopper. The spout includes an exit port that is aligned with an inlet to dosator 10.

The dosator dispenses selected amounts of particulate material transferred from the hopper utilizing a piston mechanism as described below. Specifically, dosator 10 includes a first chamber 12 aligned with the dosator inlet to receive particles gravity fed from the hopper and a second chamber 14 offset from the dosator inlet and disposed adjacent the first chamber, where the first and second chambers are separated by a dividing wall 13. The first and second chambers further communicate with each other via a channel defined between an upper end of the dividing wall and a housing wall of the dosator. A narrowed or tapered section 15 extends from a lower end of the second chamber and includes an exit port to transfer a selected dosage amount of particles from the dosator to a capsule. It is further noted that the dosator may include any selected number of suitable exit ports to effect filling of selected dosage amounts to any suitable number of capsules at a given time.

Disposed within the first chamber is a piston 16 including a stopper 17 that is vertically adjustable within the first chamber to control the first chamber volume during system operation. The piston stopper extends between dividing wall 13 and an opposing housing wall of the first chamber to provide a barrier that prevents particles that enter the first chamber from moving beyond the stopper. The piston is vertically movable by a motor or other piston control mechanism (not shown) in selected time cycles to facilitate filling of a dosage amount of particles within the first chamber and dispelling the particles from the first chamber into the second chamber and through the exit port(s) of the dosator. Specifically, a piston cycle includes vertically moving stopper 17 to a selected position within first chamber 12 so as to expose a selected volume within the first chamber for receiving and retaining particles flowing into the dosator from the hopper, followed by vertically moving the stopper toward the dosator inlet to expel particles from the first chamber into the second chamber via the passage defined between the two chambers. The particles expelled into the second chamber continue to fall through the dosator exit port(s) and into one or more open capsules disposed at the capsule station and aligned with the exit port(s) as described below.

Capsule station 30 includes a movable capsule table 32, as partially depicted in FIG. 1, to facilitate movement of open capsules 31 into aligned positions with the exit port(s) (as generally indicated by arrows 33), where movement of an open capsule 31 for filling with particles from the dosator is coordinated with the piston cycle as described above. Each open capsule preferably includes an open shell that is aligned on the capsule table with its open end facing in an upward orientation toward the dosator. The capsule table may be designed for rotary or linear movement to effect the positioning and filling of a series of capsules. In particular, when the piston is moved vertically to dispense a dosage of particles from the first chamber of the dosator into the second chamber and through the dosator exit port(s), one or more open capsules are aligned with the exit port(s) to receive the particles. As the piston is moved vertically to receive another volume of particles within the first chamber from the hopper, table 32 is moved to a position that aligns another one or more open capsules with the dosator exit port(s) to facilitate further filling of capsules. The system is further configured to manufacture a selected number of oral dosage capsules to be filled with a selected dosage amount of particles in a given time period. Upon filling of each open capsule with the selected dosage amount of particles, each filled capsule is further processed to close and seal the capsule (e.g., by combining a shell cap with the open shell of the capsule). The closing of filled capsules may occur, for example, at a location immediately downstream from the dosator filling step.

When utilizing microparticulates containing pharmaceutically active ingredients and excipient having irregular geometries and/or large sizes as described above, voids can develop in the hopper which prevent the continuous distribution and flow of particles into the dosator, which in turn results in capsules with erratic particle fill weights. In particular, a problem area (indicated by bracket 8 in FIG. 1) is defined in hopper 2 at funnel section 4. For example, irregular shaped particles disposed at this location tend to frictionally adhere to each other rather than fill in the spaces or voids formed as a result of particles having moved through the hopper and into the dosator. To overcome this problem, at least one fluid flow line 25 is inserted through a wall section of hopper 2, preferably at spout 5. The fluid flow line directs a flow of pressurized fluid (e.g., compressed air) into the hopper in a direction opposing the gravitational flow direction of the particles (indicated generally by arrow 27). A fluid flow regulator 26 is disposed on the fluid flow line to control the velocity of the fluid so as to achieve a selected velocity (e.g., a minimum fluidization velocity) for the fluid. The regulator may further be selectively controlled to generate a continuous and/or pulsated flow of gaseous fluid into the hopper during system operation. Gaseous fluid flowing into the hopper from flow line 25 fluidizes at least some of the particles disposed within problem area 8 to substantially maintain a continuous flow of particles through the hopper and substantially prevent or eliminate the formation of voids in the particle bed formed within the hopper. Accordingly, a substantially continuous and uniform flow of particles is delivered into dosator 10 and to open capsules 31 disposed at capsule station 30. While only one fluid flow line is depicted in FIG. 1, it is noted that, depending upon a particular capsule production scenario, any two or more fluid flow lines may be provided at any suitable locations within the hopper to target one or more different problem areas that may exist within the hopper based upon such scenario.

The system described above facilitates the substantially continuous and uniform flow of particles having irregular shapes and varying sizes through the hopper and dosator to produce oral dosage pharmaceutical capsules with substantially uniform blends and dosage amounts falling within an acceptable target range. In particular, production batches of oral dosage capsules are formed in accordance with the present invention in which a majority or all of the capsules in a batch contain particles that do not deviate from a desired or target fill weight by more than about 15%, and the average fill weight for a single capsule in the batch is within 10% of the target fill weight. It is noted that the term "target fill weight", as used herein, refers to establishing a substantially uniform weight for particulate matter to be filled within each capsule or other oral dosage product.

In the following Examples 1–3, an encapsulation system similar to the system described above and illustrated in FIG. 1 was utilized to prepare batches of capsules. Specifically, the encapsulation system utilized compressed air directed through a flow line and into the hopper at a sufficient velocity to establish fluidization of at least some of the particles within the hopper. These examples include particulate formulations with irregular shaped particles having a roundness value no greater than about 0.40 and granules ranging in sizes from less than Mesh 18 (i.e., greater than about 1000 $\mu$m) and greater than Mesh 35 (i.e., less than about 500 $\mu$m). While the formulation of each of these examples differs in composition, each contained about 3% by weight of an active pharmaceutical ingredient. The target fill weight for the formulation of each example was 210 mg±7%. After encapsulation, each capsule was check-weighed using a CWI-40 unit available from Shionogi & Co., LTD (New Jersey), and this unit includes five weighing stations with each station containing a micro-analytical balance. The check weight results of each example are provided below:

EXAMPLE 1

Formula PD0138-97A

| Station | Measured Number of Capsules | Capsules Within Range | Overweight Capsules | Underweight Capsules |
|---|---|---|---|---|
| 1 | 296 | 261 | 9 | 26 |
| 2 | 320 | 285 | 10 | 25 |
| 3 | 319 | 280 | 9 | 30 |
| 4 | 320 | 289 | 3 | 28 |
| 5 | 308 | 279 | 7 | 22 |

As indicated by the data presented above for this example, a total of 1563 capsules were check weighed, with 1394 capsules being within the target fill weight range and 169 capsules being out of this range. Thus, the total yield of acceptable capsules for this example was about 89%.

EXAMPLE 2

Formula PD0138-97B

| Station | Measured Number of Capsules | Capsules Within Range | Overweight Capsules | Underweight Capsules |
|---|---|---|---|---|
| 1 | 260 | 173 | 42 | 45 |
| 2 | 262 | 201 | 30 | 31 |
| 3 | 261 | 188 | 44 | 29 |
| 4 | 261 | 211 | 23 | 27 |
| 5 | 260 | 193 | 31 | 36 |

As indicated by the data presented above for this example, a total of 1304 capsules were check weighed, with 966 capsules being within the target fill weight range and 338 capsules being out of this range. Thus, the total yield of acceptable capsules for this example was about 74%.

EXAMPLE 3

Formula PD0138-97C

| Station | Measured Number of Capsules | Capsules Within Range | Overweight Capsules | Underweight Capsules |
|---|---|---|---|---|
| 1 | 229 | 191 | 33 | 5 |
| 2 | 227 | 185 | 37 | 5 |
| 3 | 223 | 190 | 31 | 7 |
| 4 | 223 | 193 | 23 | 7 |
| 5 | 226 | 167 | 52 | 7 |

As indicated by the data presented above for this example, a total of 1133 capsules were check weighed, with 926 capsules being within the target fill weight range and 207 capsules being out of this range. Thus, the total yield of acceptable capsules for this example was about 82%.

In a comparative example, an attempt was made to encapsulate each of the formulas of the above three examples utilizing the same encapsulating system but without employing pressurized fluid to fluidize particles of the particle bed within the hopper. Variation in capsule fill weight was very high when no fluidization was employed, with capsule fill weights decreasing over time as a result of voids formed within the particle bed until there was no filling at all of processed capsules. Thus, the previous examples demonstrate the effectiveness of the system and methods of the present invention for establishing a substantially continuous flow of particles having irregular shapes and sizes as described above through the hopper and dosator so as to form oral dosage pharmaceutical capsule products with acceptable fill weights.

EXAMPLE 4

During encapsulation in a batch production process, segregation of the original blend may occur with increasing production time. In particular, segregation may occur in which the particle size distribution (PSD) significantly deviates from that of the original blend, resulting in a difference of 25% or more in PSD within each respective mesh size when comparing encapsulated products with the original blend. The following example demonstrates the ability of the system and methods of the present invention to prevent segregation of a formulation blend from occurring with increasing production time.

Figure 2:
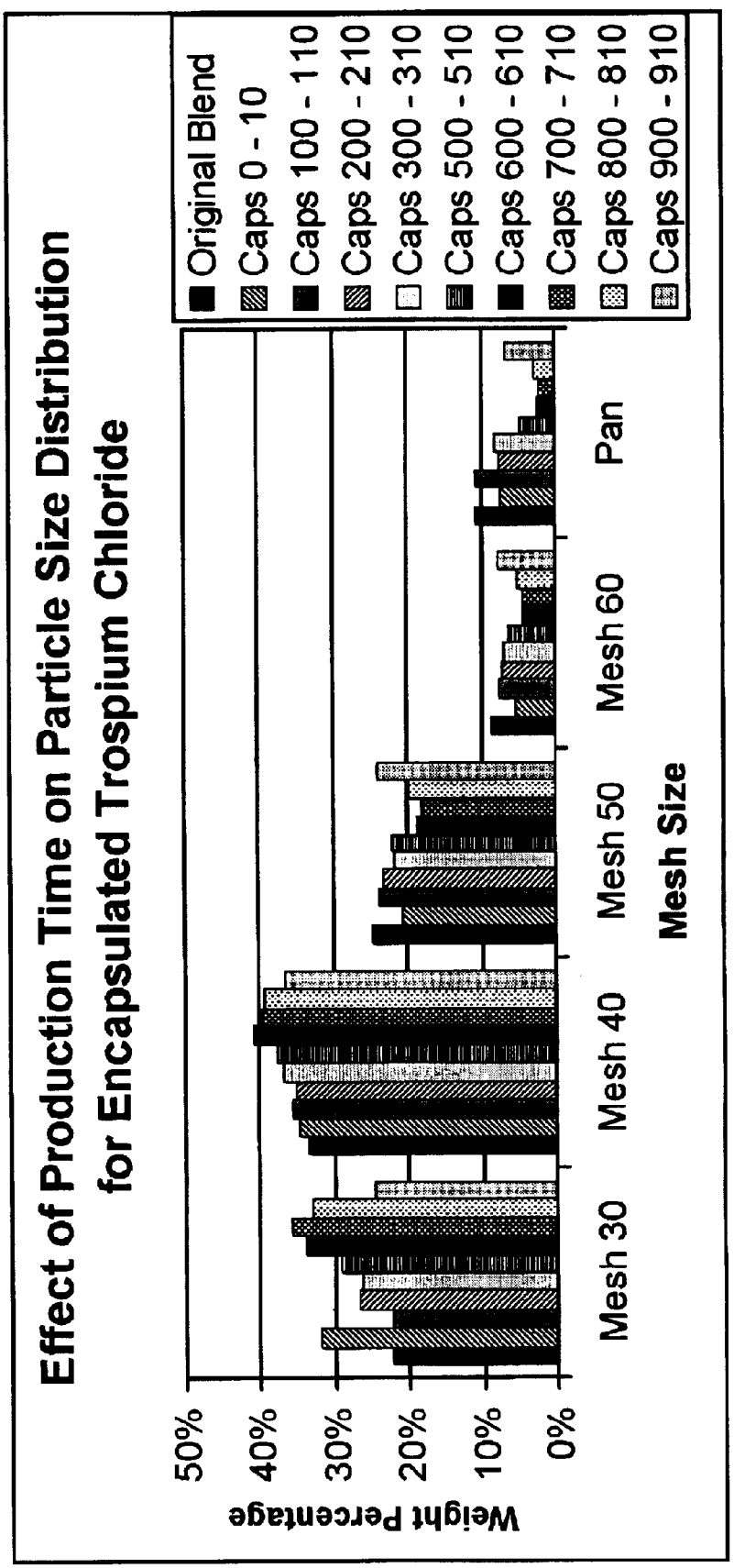
FIG. 2 is a chart illustrating the effect of time on particle size distribution for trospium chloride capsules (Formula PD0150-112) produced in accordance with the present invention.

In this example, the pharmaceutically active ingredient trospium chloride (Formula PD0151-112) was encapsulated utilizing a system substantially similar to the system described above and depicted in FIG. 1. The capsules were filled with particles having irregular geometries and a roundness value of no greater than about 0.40, with particle size dimensions ranging from about 250 $\mu$m or smaller to at least about 600 $\mu$m. The capsule production process was carried out for a time period sufficient to produce a batch containing a suitable number of capsules. Capsules from the batch were analyzed at different time periods to generate PSD vs. time data In particular, a selected number of capsules were analyzed from each sequential set of 100 capsules produced by the system, with the PSD data being generated by filtering the capsule particle content of the selected number of capsules through a series of mesh sieves and weighing the amount of particulate material contained within each sieve as well as a pan provided below the final sieve. In addition, the PSD of the original blend provided within the hopper was also analyzed for comparison with the capsule data The data obtained from this example is plotted in a bar chart depicted in FIG. 2, where the bars represent the weight percentages of particles separated into each mesh sieve and pan for the original blend and each set of capsules selected for analysis. Specifically, ten bars are associated with each mesh size unit in the chart corresponding (as indicated by the box in the chart) with the following: original blend; capsules 1–10 of the production batch; capsules 100∝110 of the production batch; capsules 200–210 of the production batch; capsules 300–310 of the production batch; capsules 500–510 of the production batch; capsules 600–610 of the production batch; capsules 700–710 of the production batch; capsules 800–810 of the production batch; and capsules 900–910 of the production batch. From the data presented in FIG. 2, it can be seen that the PSD of capsules including a blend of particles of varying sizes and produced in accordance with the present invention does not differ significantly from the PSD of the original blend. The greatest variation in PSD for this example was with larger particles captured by the Mesh 30 sieve (i.e., particles greater than about 600 µm). However, the weight percentage for particles captured by the Mesh 40, 50 and 60 sieves in each of the capsule sets remained very close to that of the original blend. Thus, this example demonstrates the effectiveness of the present invention in maintaining a substantially uniform blend of particles within the capsules during capsule production.

It will be appreciated that the embodiments described above and illustrated in the drawing represent only a few of the many ways of implementing a system and corresponding methods for fluidization of particles for encapsulation in oral dosage pharmaceutical products.

The system may be of any suitable type for producing oral dosage pharmaceutical products that includes a hopper or other suitable device to receive and transfer particles to a dosator. The dosator may be of any suitable type capable of processing particulate material greater than about 100 µm is size. The dosator may include any suitable number of outlets or exit ports for filling any selected number of capsules (e.g., one or more) or receptacles at a given time. The capsule station may be of any suitable type to facilitate the transfer of open capsules from the dosator outlet(s) to a selected area for sealing the capsules. The system may further include any selected number of hoppers, dosators and/or capsule stations to facilitate the production of a desired amount of oral dosage pharmaceutical products over a certain time period.

Any selected number of fluid flow lines may be provided to deliver one or more streams of a fluid, such as compressed air or other suitable gas, into the particle bed formed within the hopper so as to minimize or eliminate the formation of voids within the particle bed and maintain a substantially continuous and uniform flow of particles from the hopper to the dosator. For example, two or more fluid flow lines may be provided to fluidize particles at two or more locations within the particle bed within the hopper.

While the oral dosage pharmaceutical products produced in accordance with the present invention are preferably encapsulated products, it is noted that other oral dosage products may also be formed that are not encapsulated. For example, the oral dosage products may be sealed in other forms of packaging rather than capsules, where the packaging stores the particulate material prior to use of the product and is opened during use to facilitate oral delivery of the particulate material to the individual.

Having described preferred embodiments of new and improved system and corresponding methods for fluidization of particles for encapsulation in oral dosage pharmaceutical products, it is believed that other modifications, variations and changes will be suggested to those skilled in the art in view of the teachings set forth herein. It is therefore to be understood that all such variations, modifications and changes are believed to fall within the scope of the presented invention as defined by the appended claims.

What is claimed is:

1. A method of producing oral dosage pharmaceutical products utilizing a system including a hopper and a dosator disposed near an outlet of the hopper, the method comprising:
    (a) providing particulate material in the hopper, the particulate material including particles with irregular geometries as defined by a roundness value of no greater than about 0.40;
    (b) directing a gaseous fluid into the hopper to fluidize at least some of the particles within the hopper;
    (c) transferring a selected amount of the particulate material into the dosator; and
    (d) forming an oral dosage pharmaceutical product from the selected amount of the particulate material transferred into the dosator.

2. The method of claim 1, wherein the oral dosage pharmaceutical product includes a capsule containing the selected amount of the particulate material.

3. The method of claim 2, wherein (d) includes:
    (d.1) directing the selected amount of the particulate material from the dosator into the capsule.

4. The method of claim 1, wherein the particles with irregular geometries have a roundness value no greater than about 0.25.

5. The method of claim 1, wherein the particles with irregular geometries have dimensions of greater than about 100 µm.

6. The method of claim 1, wherein the particles with irregular geometries have dimensions in the range of about 125 µm and about 1,000 µm.

7. The method of claim 1, wherein the particles with irregular geometries have dimensions in the range of about 185 µm and about 400 µm.

8. The method of claim 1, further comprising:
    (e) repeating steps (c) and (d) to form a plurality of oral dosage pharmaceutical products, wherein a majority of the products formed have a weight that does not deviate from a target fill weight by more than about 15%.

9. An encapsulated oral dosage pharmaceutical product formed by the method of claim 8.

10. A batch of encapsulated oral dosage pharmaceutical products formed by the method of claim 1.

11. The method of claim 1, wherein the gaseous fluid is directed into the hopper in a direction that opposes a gravitational flow direction of the particles within the hopper.

* * * * *